Dec. 21, 1954 R. L. BYRUM Plant Pat. 1,336
ROSE PLANT
Filed Feb. 11, 1954
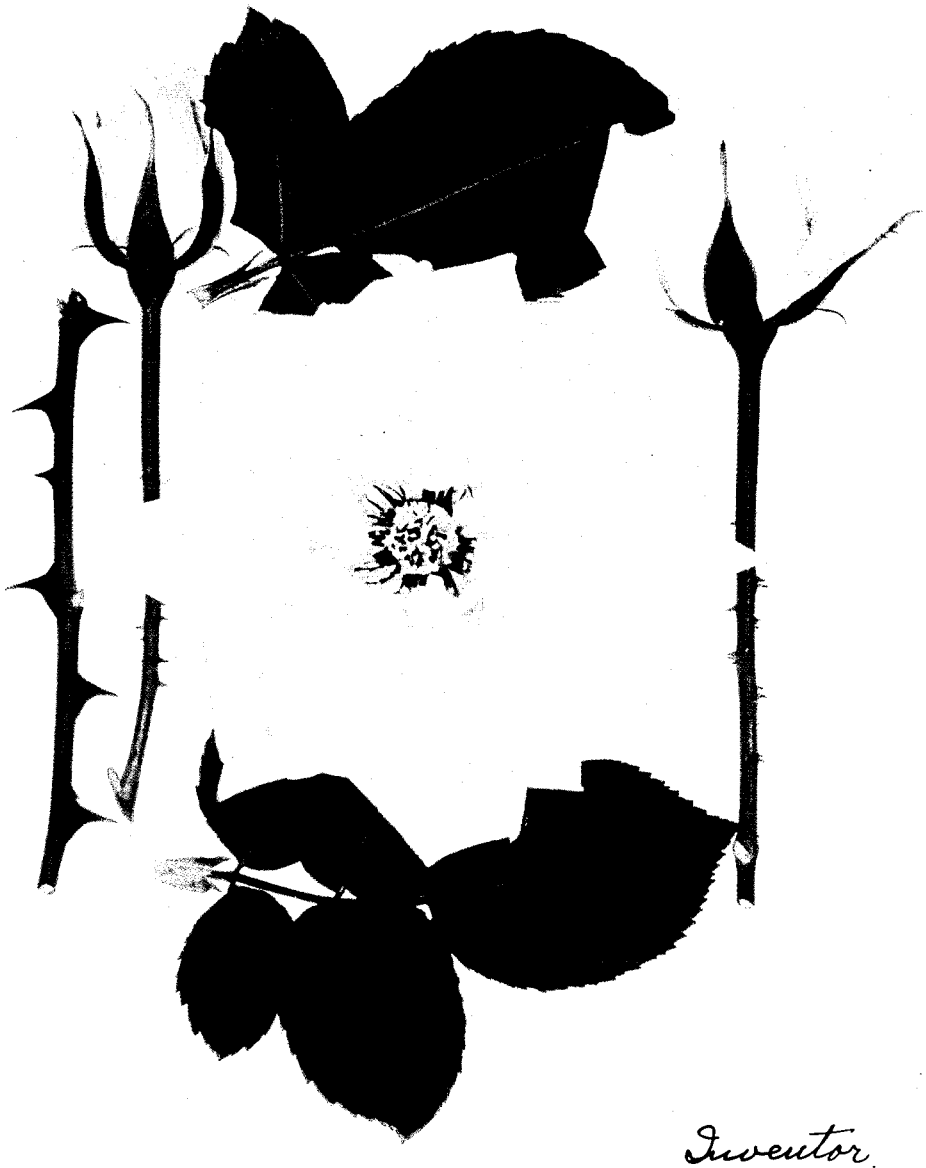
Inventor.
R. L. Byrum
By: Robb & Robb
Attorneys.

United States Patent Office

Plant Pat. 1,336
Patented Dec. 21, 1954

1,336

ROSE PLANT

Roy L. Byrum, Richmond, Ind., assignor to Joseph H. Hill Company, Richmond, Ind., a corporation of Indiana Application February 11, 1954, Serial No. 409,788

1 Claim. (Cl. 47—61)

The present invention relates to a new and distinct variety of rose plant of the hybrid tea class, which was originated by me by crossing the variety "Anzac" (Plant Patent No. 636) with the variety "Golden Rapture" (unpatented), the latter variety being more generally known in Europe as "Geheimrat Duisberg."

The primary objective in making this cross was to produce a new variety of rose which combines the characteristics of good bloom production, large size blooms of yellow color and better uniformity of color. This objective was fully achieved by selecting the variety "Golden Rapture" as the pollen parent, this variety being a very productive rose for cut-flower forcing and having very good color, and by selecting the variety "Anzac" as the seed parent, the latter variety being particularly characterized by its free blooming habit and by the relatively large size of its blooms.

As the result of the aforementioned breeding, my new variety is particularly characterized as to novelty by the combination of its relatively large flowers of amber yellow general color tonality, upright, free and vigorous growth, relatively stiff stems, semi-glossy foliage, and its retention of the large size of its flowers in hot weather when grown under glass.

The foregoing characteristics and distinctions definitely mark my new variety as a distinct improvement over its parents, as well as over all other varieties of its class.

Asexual reproduction of the new variety by both grafting and budding, as performed at Richmond, Indiana, shows that the foregoing characteristics and distinctions come true to form and are established and transmitted through succeeding propagations.

The accompanying drawing shows typical specimens of the flowers, foliage and stems of my new variety in different stages of development and depicted in color as nearly true as it is reasonably possible to make the same in a color illustration of this character.

The following is a detailed description of my new variety, based upon observations made from specimens grown in a greenhouse at Richmond, Indiana, with color terminology in accordance with Ridgway's Color Standards and Nomenclature (hereinafter abbreviated as "Ridgway"), Robert F. Wilson's Horticultural Colour Chart (hereinafter abbreviated as "Wilson"), and Koster's Color Guide (hereinafter abbreviated as "Koster"), as specifically indicated:

Type: Bush; primarily for greenhouse growing for cut-flower production.
Class: Hybrid tea.
Breeding: Seedling.
*Seed parent.*—"Anzac."
*Pollen parent.*—"Golden Rapture."
Propagation: Holds its distinguishing characteristics through succeeding propagations by both grafting and budding.

FLOWER

Flowers borne: One flower per stem; on very strong, medium length stems.
Quantity of bloom: Abundant.
Continuity: Continuous.
Fragrance: Moderate. Nature—tea.
Bud:
*Peduncle.*—Medium length; large diameter; very strong; erect.

Bark—smooth. Color—Scheele's Green, Plate 860 (Wilson).
Thorns—none.
Prickles—numerous. Color—Sap Green, Plate 62/3 (Wilson).
Hairs — few. Color — Sap Green, Plate 62/3 (Wilson).
*Before calyx breaks.*—Size—medium-large.
Form—short-pointed; with a conspicuous neck; with foliaceous appendages on the surface of the bud; with stout foliaceous parts extending beyond the tip of the bud equal to ¾ or more of its length.
Color of calyx—Scheele's Green, Plate 860 (Wilson).
*As calyx breaks.*—Color (outside of petal)—Saffron Yellow, Plate 7/1 (Wilson), with base of petal Aureolin, Plate 3/1 (Wilson); some petals shaded very lightly toward upper tip with Shrimp Red, Plate 616/2 (Wilson).
*As first petal opens.*—Size—large. Form—ovoid.
Color: Outside—Saffron Yellow, Plate 7/2 (Wilson), with base Aureolin, Plate 3/1 (Wilson), sometimes shading to Saffron Yellow, Plate 7/3 (Wilson) at upper tip of petal. Inside—Saffron Yellow, Plate 7/2 (Wilson), pencilled with Saffron Yellow, Plate 7 (Wilson), and shading to Saffron Yellow, Plate 7/3 (Wilson) at upper tip of petal.
*Opening.*—Opens up well in greenhouse; normally affected by weather conditions, but no unusual characteristics.
Bloom:
*Size (when fully open).*—Very large; from 4½ to 5 inches.
*Petalage.*—Very double; usually with no stamens showing; from 45 to 50 petals; arranged irregularly.
*Form.*—Very full, at first, but becoming open; petals being at first very tightly rolled outward, but becoming later at maturity loosely rolled outward.
*Petals.*—Thick; leathery; with inside shiny and outside satiny.
Shape—Outside petals—obovate, with apex mucronate. Intermediate petals—obovate, with apex mucronate. Inside petals—spatulate, with apex mucronate.

This description of a newly opened flower was made from a rose grown in a greenhouse at Richmond, Indiana, in the month of November:

Color of petals:
*Outside petal.*—Outside surface—Base Aureolin, Plate 3/1 (Wilson), gradually changing to Aureolin, Plate 3/3 (Wilson) up to tip; pencilled with Aureolin, Plate 3/1 (Wilson). Inside surface—Base Aureolin, Plate 3/1 (Wilson), gradually changing to Aureolin, Plate 3/3 (Wilson) up to tip; pencilled with Aureolin, Plate 3/2 (Wilson).
*Intermediate petal.*—Outside surface—Base Aureolin, Plate 3/1 (Wilson), gradually changing to Aureolin, Plate 3/3 (Wilson) up to tip. Inside surface—Base Aureolin, Plate 3/1 (Wilson), gradually changing to Aureolin, Plate 3/3 (Wilson) up to tip; lightly pencilled with Aureolin, Plate 3/2 (Wilson).
*Inner petal.*—Outside surface—Base Aureolin, Plate 3/1 (Wilson), gradually changing to Aureolin, Plate 3/3 (Wilson) up to tip. Inside surface—Base Aureolin, Plate 3/1 (Wilson), gradually changing to Aureolin, Plate 3/3 (Wilson) up to tip; lightly pencilled with Aureolin, Plate 3/2 (Wilson).

This description was made from a rose that was open for three days in a greenhouse at Richmond, Indiana, in the month of November:

Color of petals:
*Outside petal.*—Outside surface — Base Aureolin, Plate 3/2 (Wilson), gradually changing to Aureolin, Plate 3/3 (Wilson) at tip. Inside surface—

Base Aureolin, Plate 3/1 (Wilson), changing through Aureolin, Plate 3/2 (Wilson) to Aureolin, Plate 3/3 (Wilson) at tip.

*Intermediate petal.*—Outside surface—Base Aureolin, Plate 3/2 (Wilson), changing to Aureolin, Plate 3/3 (Wilson) at tip. Inside surface—Base Aureolin, Plate 3/1 (Wilson), changing through Aureolin, Plate 3/2 (Wilson) to Aureolin, Plate 3/3 (Wilson) at tip.

*Inner petal.*—Outside surface—Base Aureolin, Plate 3/2 (Wilson), changing to Aureolin, Plate 3/3 (Wilson) at tip. Inside surface—Base Aureolin, Plate 3/1 (Wilson), changing through Aureolin, Plate 3/2 (Wilson) to Aureolin, Plate 3/3 (Wilson) at tip.

General color effect of open bloom:

*Newly opened flower.*—Amber Yellow, Plate 505 (Wilson).

*Three days open.*—Amber Yellow, Plate 505/1 (Wilson).

Behavior of petals: Persist; normally affected by weather conditions, but no unusual characteristics; color fading to Aureolin, Plate 3/3 (Wilson).

Flower longevity: Cut roses grown in greenhouse and kept at living-room temperatures—4 or 5 days in July.

PLANT

Foliage:

*Leaves.*—Compound of 5 leaflets; very abundant; very large; very heavy; semi-glossy; wrinkled.

*Leaflets.* — Shape — ovoid. Apex — mucronate. Base—round. Margin—simply serrate.

*Color.*—Mature: upper surface—near Spinach Green, Plate 0960 (Wilson); under surface—near Apple Green, Plate No. 77 (Koster). Young: upper surface—Lettuce Green, Plate No. 74 (Koster), overlaid with shadings of Indian Red, Plate XXVII (Ridgway); under surface—Lettuce Green, Plate No. 74 (Koster), overlaid with shadings of Indian Red, Plate XXVII (Ridgway).

*Rachis (the supporting stem of the compound leaf).*—Heavy.

Upper side—grooved.

Under side—smooth.

*Stipules.*—Moderately short; medium width; with short points turning out at an angle of less than 45°.

Growth:

*Habit.*—Bush; upright; much-branched.

*Growth.*—Free; vigorous.

*Canes.*—Large diameter.

*Main stems.*—Color—Spinach Green, Plate 0960/1 (Wilson); some mixed with Deep Brownish Drab, Plate XLV (Ridgway).

Thorns—many; medium length; hooked downward; with long base. Color—Red Ochre, Plate No. 94 (Koster).

Prickles—very few. Color—Red Ochre, Plate No. 94 (Koster).

Hairs—none.

*Branches.*—Color—Spinach Green, Plate 0960/1 (Wilson).

Thorns—many; long; hooked downward; with long base. Color—Sap Green, Plate 62/3 (Wilson), overlaid with Violet Lilac, Plate No. 47 (Koster); a few are shades of Sap Green, Plate 62/3 (Wilson) mixed with Violet Lilac, Plate No. 47 (Koster).

Prickles—few. Color—Sap Green, Plate 62/3 (Wilson).

Hairs—none.

*New shoots.*—Color—Lettuce Green, Plate No. 74 (Koster).

Thorns—many; medium length; hooked downward; with long base. Color—Amaranth Red, Plate No. 43 (Koster).

Prickles—none.

Hairs—none.

REPRODUCTIVE ORGANS

Stamens: Many; arranged regularly about pistils.

Filaments: Medium length; most with anthers. Color—Spinel Red, Plate 0023/1 (Wilson).

Anthers: Small; all open at once. Color—Maize Yellow, Plate 607/2 (Wilson).

Pollen: Abundant. Color—Maize Yellow, Plate 607/3 (Wilson).

Pistils: Medium number.

Styles: Uneven; medium length; moderately thin; bunched. Color—Rose Madder, Plate 23/2 (Wilson).

Stigma: Color—white.

Ovularies: All encased in receptacle.

Sepals: Permanent; medium length; spear-shaped. Color: inside—Scheele's Green, Plate 860/3 (Wilson), overlaid with Pod Green, Plate 861/3 (Wilson); outside—Scheele's Green, Plate 860/1 (Wilson).

I claim:

A new and distinct variety of rose plant of the hybrid tea class, substantially as herein shown and described, characterized particularly as to novelty by the combination of its relatively large flowers of amber yellow general color tonality, its upright, free and vigorous growth, its relatively stiff stems, its semi-glossy foliage, and its retention of the large size of its flowers in hot weather when grown under glass.

No references cited.